United States Patent [19]
Simoes

[11] Patent Number: 6,045,360
[45] Date of Patent: *Apr. 4, 2000

[54] INSTRUMENT FOR THE MEDICAL OR DENTAL TREATMENT OF CHILDREN

[76] Inventor: Dionisio Rio Simoes, Rua 5 de Outubro, N° 71, P-8200, Albufeira, Portugal

[ * ] Notice: This patent issued on a continued prosecution application filed under 37 CFR 1.53(d), and is subject to the twenty year patent term provisions of 35 U.S.C. 154(a)(2).

[21] Appl. No.: 09/135,486

[22] Filed: Aug. 18, 1998

[51] Int. Cl.[7] ........................................................ A61C 3/00
[52] U.S. Cl. ............................ 433/141; 433/147; 15/167.1
[58] Field of Search ...................................... 433/141, 143, 433/144, 147, 29, 77; 15/167.1, 145; D4/107, 125; 600/200, 104, 139; 446/72, 27

[56] References Cited

U.S. PATENT DOCUMENTS

| | | | |
|---|---|---|---|
| D. 113,743 | 3/1939 | Kahn | D4/107 |
| 5,038,755 | 8/1991 | Burgio et al. | 600/200 |
| 5,187,829 | 2/1993 | Atkins | 15/167.1 |
| 5,353,464 | 10/1994 | Atkins et al. | 15/167.1 |
| 5,774,921 | 7/1998 | Harrison et al. | 15/145 |

*Primary Examiner*—Gene Mancene
*Assistant Examiner*—Pedro Philogene
*Attorney, Agent, or Firm*—Jones, Tullar & Cooper, P.C.

[57] ABSTRACT

An instrument for the medical or dental treatment of children having a treatment element with a tool at one end and a handle with a free end to which a toy element is fastened. The toy element is provided with at least one toy which is visible by the children during treatment.

19 Claims, 4 Drawing Sheets

INSTRUMENT FOR THE MEDICAL OR DENTAL TREATMENT OF CHILDREN

FIELD OF THE INVENTION

The present invention relates to an instrument for the medical or dental treatment of children, having a treatment element, which has a tool and a handle adjoining the latter.

BACKGROUND OF THE INVENTION

Many children become so scared by medical treatment as such, and in particular by the shining chromed medical instruments, that they refuse all cooperation in the healing treatment or in preventive treatment of illnesses. On the one hand, this makes it difficult for a physician to deal with his small patients. On the other hand it is also difficult to introduce the children to medical treatment or preventive measures for health care in the private sphere. Therefore physicians and parents need to take pedagogic steps to free children of this fear.

SUMMARY OF THE INVENTION

It is therefore an object of the present invention to further develop a device of the above mentioned type in a way which does not act as a deterrent to children, but still fully meets the intended functions.

The attainment consists in that the instrument has a toy element with a least one toy at the free end of the handle.

By means of the "child-friendly designed instrument" in accordance with the present invention, the children are on the one hand distracted by play, so that their fear of medical treatment is at least reduced. By removal of the fear of the children, the device of the present invention simultaneously fulfills a pedagogic purpose, since the children are introduced to medical treatments and health care without fear or rejection even arising.

In an advantageous manner the toy element can be removed from the toy and/or from the handle of the treatment element. In this way both parts can be produced separately and freely combined with each other.

It is of advantage for the handling ease of the instrument in accordance with the present invention, if the toy element is connected with the handle of the instrument via an extension element, because this gives the physician greater freedom of movement, so that the additionally attached toy element does not interfere with the treatment. An elastic element on the toy element, or respectively on the toy, for example in the form of a spring, serves the same purpose. In addition, a jiggling, moving toy distracts the children even more and perhaps even encourages them to play, without the treating physician needing to interrupt his treatment every time.

The type of toy is completely optional and depends on personal preferences, but also on the ease of handling, so that an upper limit must be assumed regarding the size of the toy element. Otherwise the designer is free to choose. For example, it is possible to make use of representations of animals, fairy tale figures, figures from comics or animated films, whose popularity with children is also a matter of fashions.

For hygienic reasons the elements of the instrument are preferably made of plastic material or hard rubber, wherein there are no limitations placed on the material used. Which plastic material, or respectively which hard rubber is used is primarily a fuiction of the use of the instrument, i.e. how hard and resistant, or respectively how flexible it needs to be.

Instruments made of plastic material or hard rubber are mostly disposable materials, which are subsequently discarded. In this case the use of hard rubber has the advantage that the disposal is simpler from the viewpoint of ecology. But the actual treatment element, or respectively the extension element, can also be made of metal, so that they can be sterilized and used again. This reveals another particular advantage of the multi-part design of the instrument in accordance with the present invention, i.e. the fact that after each treatment the toy element can be separated from the actual treatment element and fastened again on a new treatment element. It is possible to connect the instruments in accordance with the present invention in the way they are actually needed and in this way they can be adapted to any type of treatment—and also to the preferences of the children.

Depending on the design, all elements, even the toy element, can be conceived as disposable articles.

Basically the instrument in accordance with the present invention is suitable for all medical and dental treatments of children. It is particularly designed for instrument which are themselves relatively small and which generate a definite fear in children. Examples are in dentistry the many dental instruments, but also instruments which are used by an ophthalmologist, or an ear, nose and throat specialist, or the family physician.

An exemplary embodiment of the present invention will be described in more detail in what follows by means of the attached drawings.

DESCRIPTION OF THE PREFERRED EMBODIMENTS

Figure 1A:
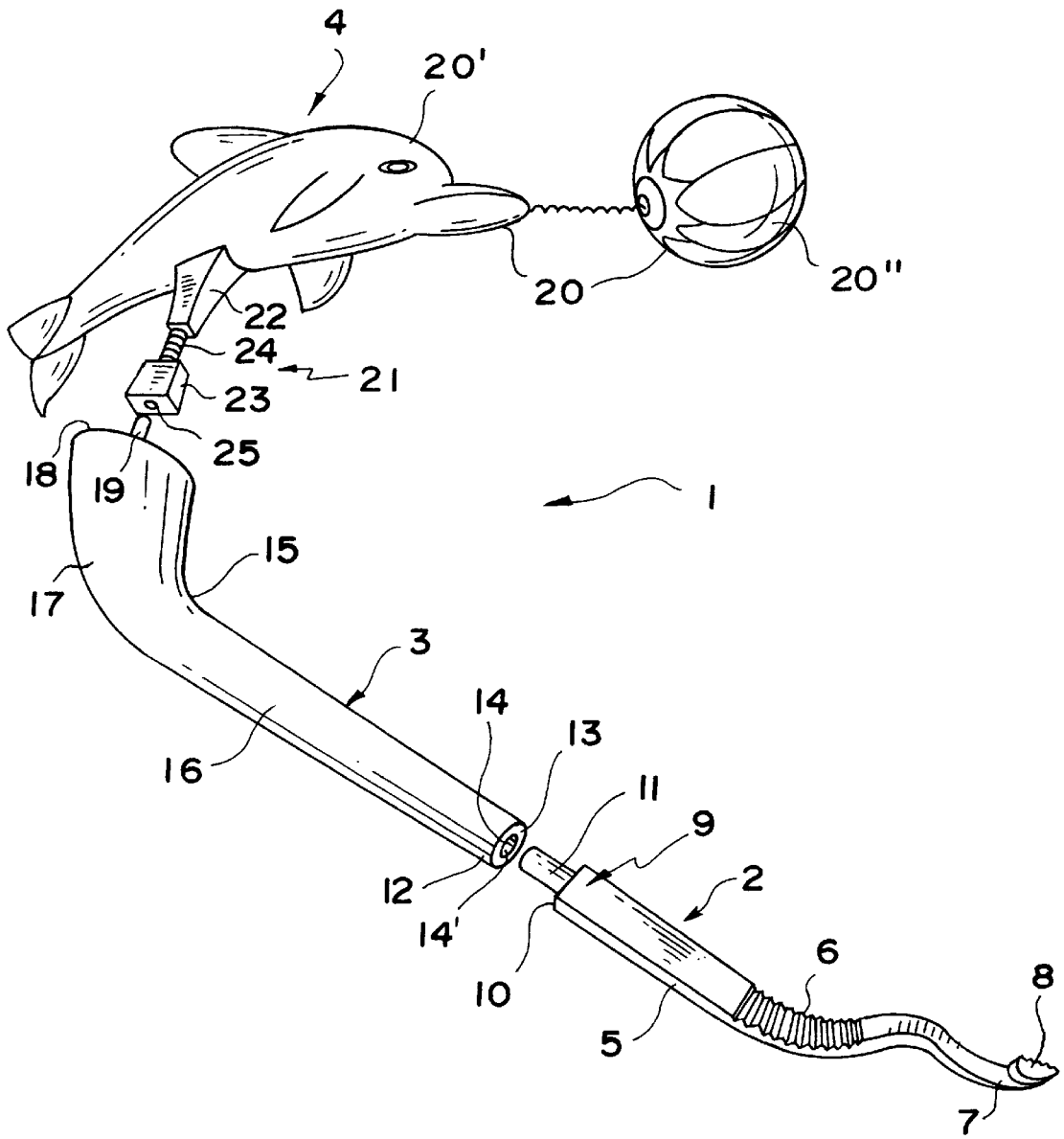
FIG. 1a, an instrument in accordance with the present invention in an exploded view is shown.

The present invention will be described in what follows by means of an example of dental instruments for children. However, this is not intended as a limitation to such instruments. It is possible to design instruments of all types in accordance with the present invention.

In the exemplary embodiment, the instrument 1 in accordance with the present invention consists of three parts. Besides the actual treatment element 2, it has an extension element 3 and a toy element 4. Here, the extension element 3 is not an absolutely required component, but it is advantageous for placing the toy element 4 at a greater distance from the treatment element 2, so that the physician is not being hampered in his work.

The treatment element 2 essentially consists of a bent or kinked handle 5 with grooves 6 for better handling. At its end 7, the handle 5 ends in the actual tool 8, here for dental treatment. The handle 5 tapers here in the direction toward the tool 8. Therefore the somewhat thicker free end 9 of the handle 5 has a flat front face 10, to the center of which a cylindrical cap 11 has been applied. In this case, the cap 11 is of one piece with the handle 5.

The extension element 3 is plugged into the treatment element 2. On its lower free end 12 the extension element 3 has a circular diameter. The free end 12 constitutes a front face 14 having a bore 14', whose diameter is of such a size that the cap 11 at the free end 9 of the handle 5 of the treatment element 2 fits exactly into it and is clampingly held. The diameter of the extension element 3 is slightly increased from its lower free end 12 to a kink 15, where it is laterally kinked at an angle of approximately 40°. From this a long leg 16, circular in cross section, a short leg 17 is created. with respect to the long leg 16, the short leg 17 has a considerably increased diameter and is no longer circular, but oval in cross section. It terminates in an end face 18, on which a cap 19 is also formed. As in the present exemplary embodiment, this cap can also be cylindrical, can be arranged at the center or off-centered and can have various diameters. However, an off-centered arrangement is preferred, as well as the embodiment as a relatively thin pin, as represented in the exemplary embodiment. This has the advantage that the toy element 4, which is to be placed on the cap 19 is arranged slightly laterally with respect to the axis of the short leg 17, so that it is less in the way of the treatment by the treating physician.

The toy element 4 in turn is placed on the cap 19 of the handle element 3. In the present case the toy element 4 is a toy 20 in the shape of a dolphin 20' and a ball 20". A connecting element 21 has been applied to the toy 20, in the exemplary embodiment on the belly side of the dolphin 20', which has an upper segment 22 on the side toward the toy, and a lower segment 23 on the side toward the instrument. The segments 22 and 23 are connected with each other by a helical spring 24, so that the toy element 4 is provided with some degree of elasticity and mobility with respect to the movements of the treatment element 1 in the hand of the physician, and possibly the grasp of the child. The lower segment 23 of the connecting element 21 is provided with a bore 25, whose diameter in turn has been matched to the cap 19 of the extension element 3, so that the connecting element 21 can be plugged in and clampingly held in place.

Figure 1B:
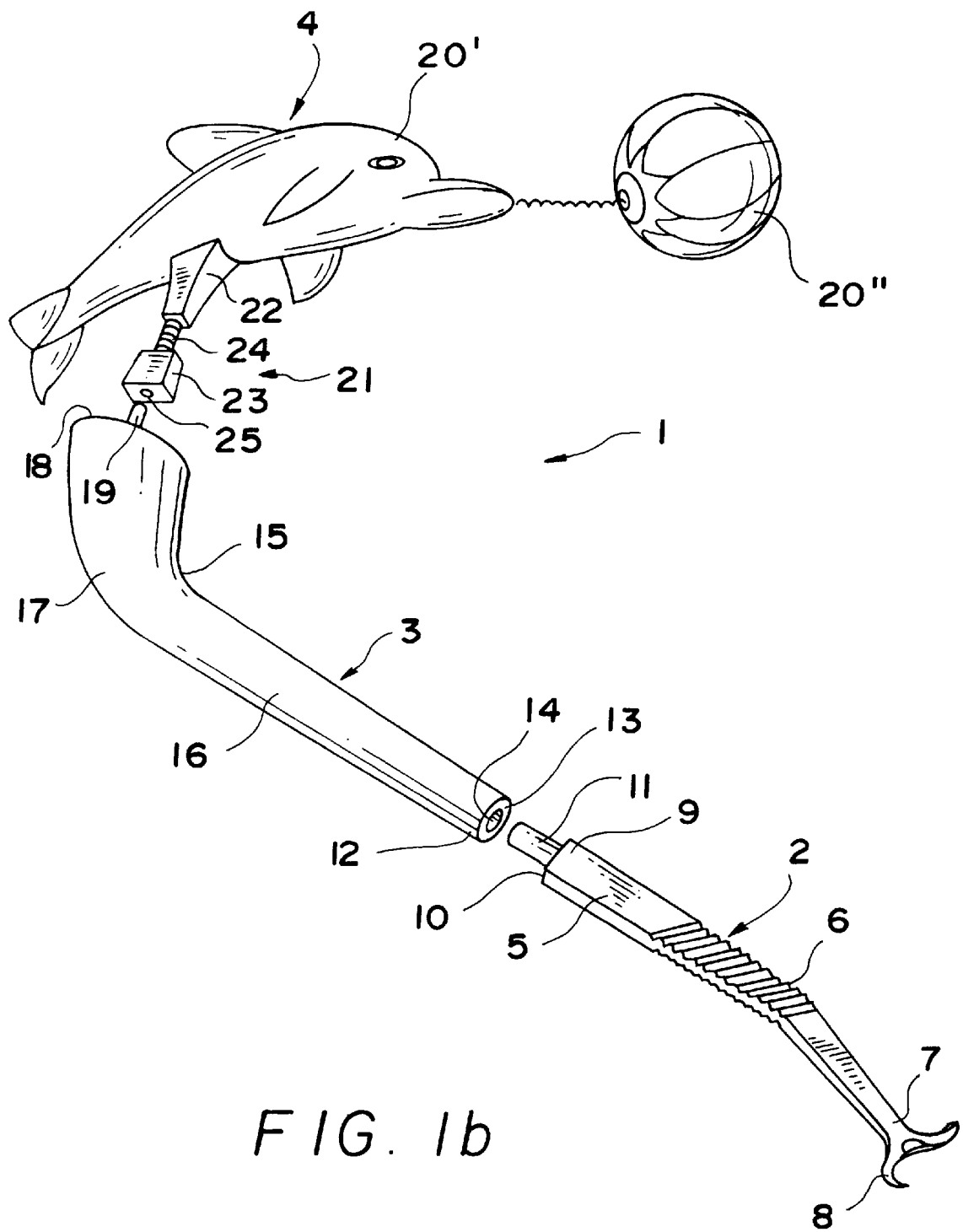
FIG. 1b, another instrument in accordance with the present invention in an exploded view is shown.

The embodiment shown in FIG. 1b differs from the embodiment shown in FIG. 1a in that the tool 8 is different. It shows the treatment element of FIG. 2b.

Figure 2A:
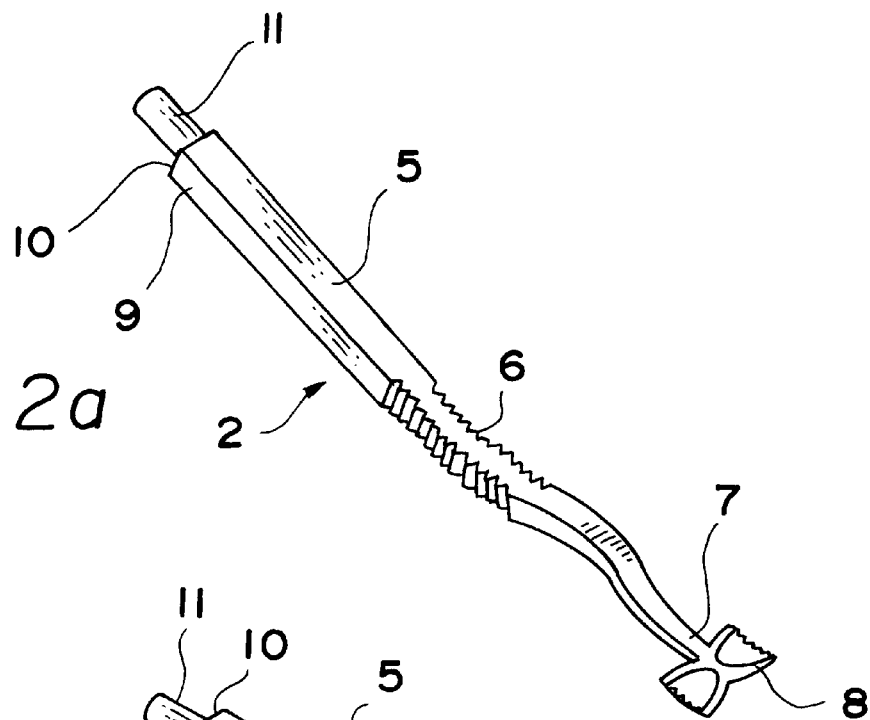
FIGS. 2a to 2e, show, by way of example, some treatment elements for the dental treatment of children.
Figure 2B:
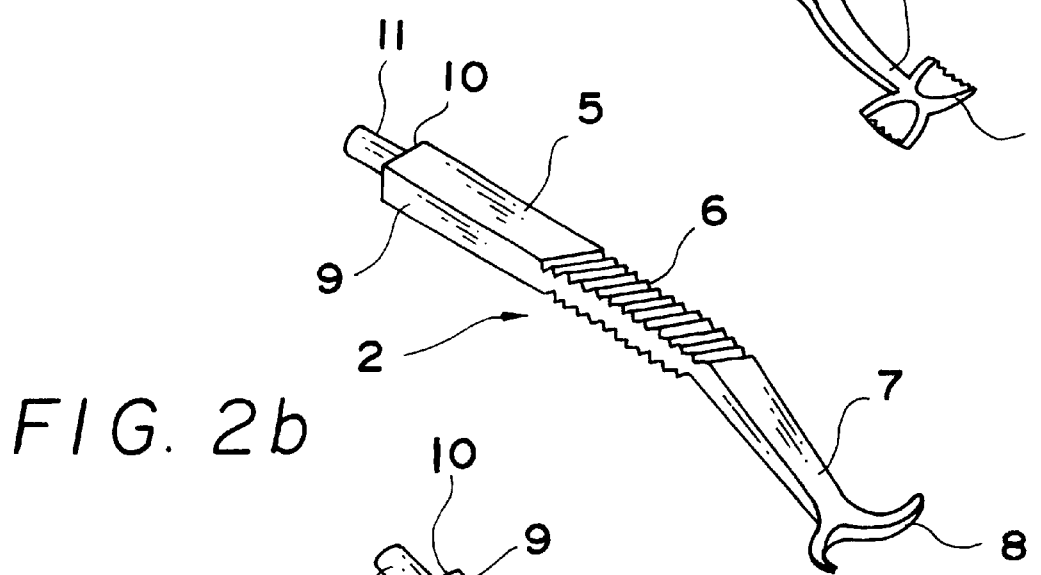
Figure 2C:
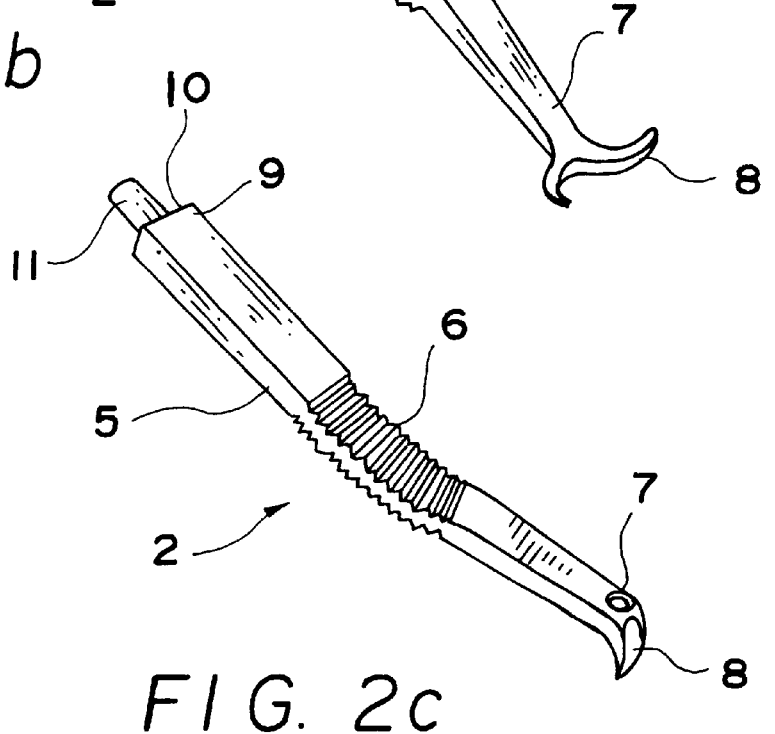
Figure 2D:
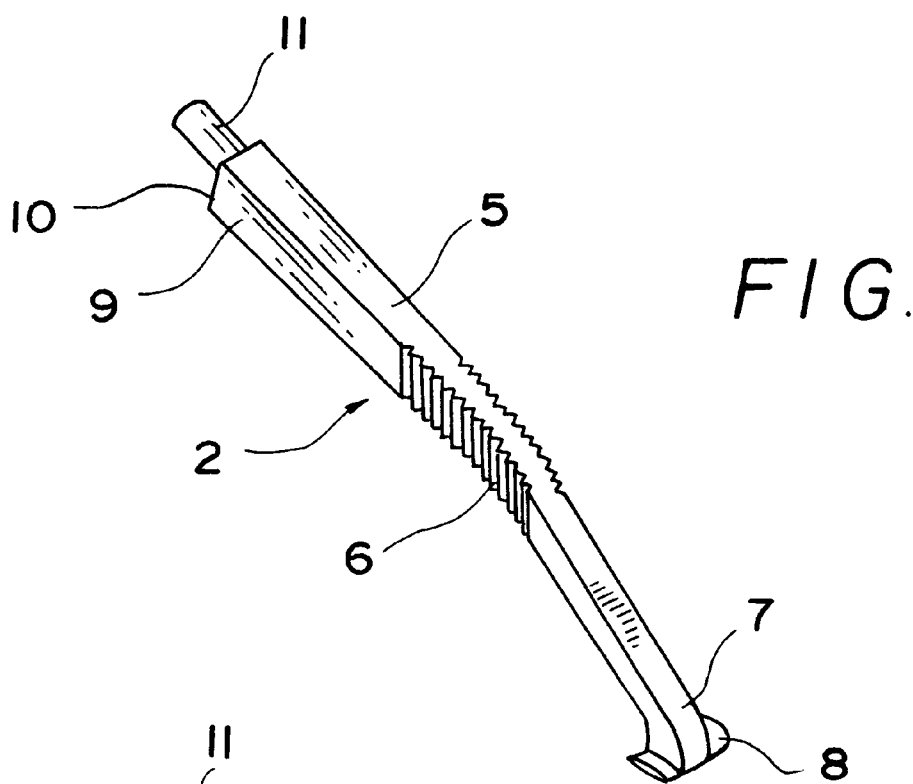
Figure 2E:
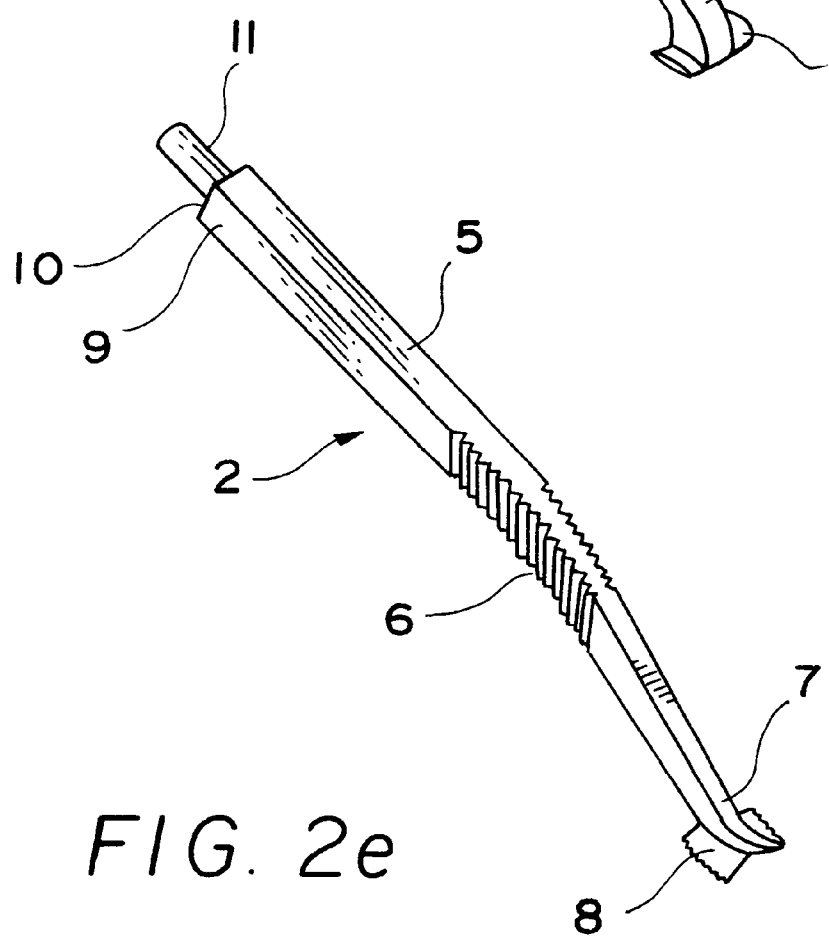

Some dental instruments for children have been represented merely by way of example in FIGS. 2a to 2e, which have been designed in accordance with the present invention as the treatment element 2 of the instrument. The treatment element represented in FIG. 2a is used for treating the teeth, not shown, in the upper jaw of children in the age group between 6 and 7 years. The treatment element represented in FIG. 2b is used for treating the teeth not shown, in the lower jaw of children in the age group between 9 and 10 years. The treatment element represented in FIG. 2c is used for removing remaining roots in the upper jaw and lower jaw, while the treatment elements represented in FIGS. 2d and 2e are used for treating the molars of children in the age group between 9 and 10 years.

Common to all these treatment elements is the design in the form of a handle 5, which is ergonomically shaped and provided with grooves 6. The handle 5 makes a transition on the one end into the actual tool 8, and on its free end 9 the handle terminates in a front face 10, which has the cap 11 for plugging in the extension element 3.

What is claimed is:

1. An instrument for at least one of a medical and dental treatment of children, comprising:
   a treatment element including a tool and a handle adjoining the tool, said handle having a free end;
   a connecting element; and
   a toy element fastened to said free end by said connecting element, said toy element comprising at least one toy.

2. The instrument as defined in claim 1, wherein said connecting element is removably fastened on said free end.

3. The instrument as defined in claim 1, further comprising:
   an extension element fastened between said free end and said connecting element.

4. The instrument as defined in claim 3, wherein said extension element is removably fastened on one of said handle; said connecting element and said handle; and said connecting element.

5. The instrument as defined in claim 1, further comprising:
   at least one elastic element as part of said connecting element, wherein said toy element is connected to said at least one elastic element.

6. The instrument as defined in claim 3, wherein said treatment element, said toy element and said extension element are made of plastic.

7. The instrument as defined in claim 3, wherein said treatment element, said toy element and said extension element are made of hard rubber.

8. The instrument as defined in claim 3, wherein at least one of said treatment element and said extension element are made of metal, and said toy element is made of one of plastic and hard rubber.

9. The instrument as defined in claim 1, wherein said treatment element is in the form of an instrument for the dental treatment of children.

10. The instrument as defined in claim 1, wherein said treatment element is in the form of an instrument for throat, nose and ear medicine.

11. The instrument as defined in claim 1, wherein said treatment element is in the form of an instrument for ophthalmology.

12. The instrument as defined in claim 1, wherein said treatment element is in the form of an instrument for general medicine.

13. The instrument as defined in claim 1, wherein said treatment element has an end opposite to said free end, and wherein the tool is located at said opposite end, the toy being visible to the children during treatment.

14. The instrument as defined in claim 3, wherein said extension element has an end opposite to said free end, and wherein the tool is located at said opposite end, the toy being visible to the children during treatment.

15. The instrument as defined in claim 1, wherein said connecting element includes an elastic member allowing said toy element to move relative to said treatment element.

16. The instrument as defined in claim 15, wherein said elastic member is a spring.

17. The instrument as defined in claim 16, wherein said connecting element further includes an upper segment for connection to said toy element and a lower section for connection to said treatment element, and wherein said spring is situated between said upper section and said lower section.

18. The instrument as defined in claim 16, further comprising:
   an extension element, wherein said connecting element further includes an upper segment for connection to said toy element and a lower section for connection to said extension element, said extension element further being connected to said treatment element.

19. The instrument as defined in claim 18, wherein said extension element includes two legs oriented together to form an angle.

* * * * *